United States Patent [19]
Drakoff

[11] 3,964,500
[45] June 22, 1976

[54] LUSTERIZING SHAMPOO CONTAINING A POLYSILOXANE AND A HAIR-BODYING AGENT

[75] Inventor: Raymond Drakoff, New York, N.Y.

[73] Assignee: Lever Brothers Company, New York, N.Y.

[22] Filed: June 18, 1975

[21] Appl. No.: 588,120

Related U.S. Application Data

[63] Continuation of Ser. No. 428,288, Dec. 26, 1973, abandoned.

[52] U.S. Cl. ............................ 132/7; 252/DIG. 2; 252/DIG. 3; 252/DIG. 13; 252/542; 252/550; 252/551; 424/DIG. 2; 424/70; 424/78; 424/81; 424/180; 424/362
[51] Int. Cl.² ........................................... A61K 7/06
[58] Field of Search ....... 132/7; 424/70, 71, DIG. 2; 252/DIG. 2, DIG. 3, DIG. 13, 542, 550, 551

[56] References Cited
UNITED STATES PATENTS

| | | | |
|---|---|---|---|
| 3,198,747 | 8/1965 | Cook et al. | 252/389 |
| 3,208,911 | 9/1965 | Oppliger | 424/70 |
| 3,392,040 | 7/1968 | Kass | 424/70 |
| 3,562,786 | 2/1971 | Bailey et al. | 252/137 |
| 3,580,853 | 5/1971 | Parran | 424/70 X |

FOREIGN PATENTS OR APPLICATIONS

| | | | |
|---|---|---|---|
| 1,362,179 | 4/1964 | France | 424/70 |
| 8,757 | 8/1906 | Netherlands | 424/70 |

*Primary Examiner*—V. D. Turner
*Assistant Examiner*—Vera C. Clarke
*Attorney, Agent, or Firm*—Kenneth F. Dusyn; Arnold Grant

[57] ABSTRACT

Undesirable effects, such as heaviness, oiliness and stringiness, accompanying the deposition of lusterizing amounts of polydimethylsiloxane on the hair during shampooing are reduced or overcome without substantially affecting luster by the presence in the shampoo composition of a polymeric hair bodying agent. The polymeric hair bodying agent also possesses the property of increasing the amount of polydimethylsiloxane deposited on the hair.

16 Claims, No Drawings

LUSTERIZING SHAMPOO CONTAINING A POLYSILOXANE AND A HAIR-BODYING AGENT

This is a continuation of application Ser. No. 428,288, filed Dec. 26, 1973, now abandoned.

BACKGROUND OF THE INVENTION

1. Field of the Invention

The present invention relates to a hair lusterizing shampoo containing an anionic or amphoteric surfactant foaming agent, a lusterizing agent which is a polydimethylsiloxane, and a hair bodying polymeric resin which is soluble in water or solubilized in the aqueous shampoo product.

Polydimethylsiloxanes having relatively low viscosities, for example about 25 centistokes or less, have poor adhesiveness on the hair when applied to the hair from a shampoo composition and have substantially no hair-grooming properties. On the other hand, the polydimethylsiloxanes useful in the practice of the present invention, i.e., those having viscosities of about 1,000 to about 2,500,000 centistokes, are effective hair-grooming agents when heavily deposited on the hair, but introduce problems of heaviness, oiliness, and stringiness. When an excessive amount of a siloxane has been deposited on the hair, many hair styles become difficult to achieve. Overconditioned hair tends to lie flat and to be slick.

The aforementioned resin not only performs the function of a hair-bodying agent, but cooperates with the polydimethylsiloxane to reduce the oiliness, heaviness and stringiness of the hair imparted by the siloxane and to increase the amount thereof deposited on the hair.

2. The Prior Art

Shampoo compositions containing water-insoluble polydimethylsiloxane are well known in the art, as illustrated by the disclosures in U.S. Pat. No. 2,826,551 assigned to the Simoniz Company.

As a further illustration of the use of polysiloxanes in hair care products reference may be made to an article by Charles W. Todd and Steven Hayes in "Americn Perfumer and Cosmetics", Volume 86, pages 112–114, October, 1971. In this article the authors disclose the use of silicones to relieve the stickiness of the resins in a hair spray.

U.S. Pat. No. 3,215,603 discloses the use in hair-grooming compositions of a copolymer of a low molecular weight olefin and maleic anhydride cross linked with vinyl crotonate.

U.S. Pat. No. 2,415,389 describes a method for the preparation of alkoxy end-blocked polysiloxanes.

SUMMARY OF THE INVENTION

It has now been discovered that the oiliness, heaviness, and stringiness imparted to hair shampooed with a foaming composition containing a water-insoluble polydimethylsiloxane lusterizing agent is greatly reduced or overcome by the presence in the composition of a polymeric hair-bodying agent. Additionally the polymeric hair-bodying agent increases the amount of polydimethylsiloxane deposited on the hair.

It is an object of the present invention to formulate a shampoo having a lusterizing effect on the hair without any attendant oiliness, heaviness, and stringiness.

It is another object of the invention to enhance the deposition of a polydimethylsiloxane lusterizing agent on the hair during a shampoo operation.

Accordingly in its broadest aspect, the invention provides a foaming shampoo composition which contains a water-insoluble polydimethylsiloxane lusterizing agent and a polymeric hair bodying agent, which, in addition to its known function of providing body to the hair greatly reduces the aforesaid oiliness, heaviness and stringiness imparted to the hair by the polydimethylsiloxane and additionally co-acts to increase the amount of the polysiloxane deposited on the hair.

In a broad embodiment of the invention there is provided a shampoo composition comprising:
  i. an anionic or amphoteric foaming detergent surfactant,
  ii. a water-insoluble polydimethylsiloxane having hair-lusterizing properties and having a viscosity of about 1,000 to about 2,500,000 centistokes measured at 25°C, and mixtures thereof,
  iii. a hair bodying agent, which is a polymeric resinous substance, and
  iv. water, which may contain up to about its own weight of ethanol.

DETAILED DESCRIPTION OF THE INVENTION

The surfactant, which is a compound capable of producing a desired level of foam and of having a good detergent action on the hair when used as a shampoo, may be present in the composition in proportions of about 5% to about 25%, whole composition basis. The surfactants within the meaning employed in the instant specification are free of silicon in their molecular structure.

The polydimethylsiloxane may be present in the composition in proportions of about 3% to about 60%, and the hair-bodying agent in proportions of about 1% to about 25%, whole composition basis.

The solvent will comprise about 30% to about 91% of the composition by weight, and may comprise 0% to about 50% ethanol by weight of the solvent, the balance, about 50% to 100%, being water.

The shampoo compositions of the invention impart good groom and brilliantine effects to the hair, and eliminate or greatly reduce comb resistance. The polydimethylsiloxane component is chemically stable in the shampoo medium, is safe for external use, has very little adverse effect on lather volume, and does not affect hair dyeing or cold waving.

By the term "bodying" as applied to the hair is meant the conferring thereupon of a feeling of thickness or substance manifested by improved control during combing, shaping, or teasing. The consumer may preceive this as an increase in combing resistance or drag on the hair either in the wet or dry state. Physically, the interfiber friction of hair has been increased.

To achieve a desired level of gloss or luster on the hair, the shampoo may contain relatively large amounts of a low viscosity polydimethylsiloxane or a relatively small amount of a high viscosity polydimethylsiloxane. For example, no luster improvement is obtained in vitro with a shampoo containing up to 50% of its weight of a polydimethylsiloxane having a viscosity of 100 centistokes although an improvement in luster is noted at a level of 50% when the polydimethylsiloxane has a viscosity of 5,000 centistokes. Also, an improvement is noted when the shampoo contains only 10% of a polydimethylsiloxane having a viscosity of 30,000 centistokes.

Viscosities of the polydimethylsiloxanes useful in the practice of the present invention are within the range of about 1,000 to about 2,500,000 centistokes, preferably about 5,000 to about 60,000 centistokes, measured at 25°C. Average molecular weights range broadly from about 17,000 to about 180,000, preferably from about 30,000 to about 52,000.

The presence of a bodying agent counteracts the lubricity of the hair imparted by the polydimethylsiloxane, but ordinarily does not significantly decrease the luster, and the combination thereby imparts visual luster with substantially no tactile feel of oiliness.

The reason for the enhancing effect of the hair-bodying resin on the lusterizing and deposition characteristics of the polydimethylsiloxane is not known. While not wishing to be held to any theory, it is believed that the hair-bodying resin precipitates upon dilution of the shampoo composition and application to the hair, whereupon the resin coacervates with the siloxane and the coacervate deposits on the hair strands.

In use, the hair is washed with a shampoo composition within the instant invention, the washing being carried out by simple shampoo procedures, usually with a diluted product, generating a foam on the hair, preferably by movement of the hands and fingers, then rinsed with water to remove substantially all foaming components from the hair. By these steps, and provided that the shampoo contains at least one of the polydimethylsiloxanes and one of the hair-bodying agents described hereinafter, the polydimethylsiloxane is deposited on the hair in an amount at least sufficient to impart visual luster with substantially no tactile feel of oiliness.

The compositions of the invention may be in the form of pourable, turbid liquids, or may be gels, or may be two-phase liquids having the polysiloxane in the upper layer.

Liquid forms of the product of the invention may contain about 5% to about 25% surfactant, about 3% to about 50% polysiloxane having a viscosity of about 1,000 to about 2,500,000 centistokes at 25°C, and about 1% to about 10% of a polymeric resinous hair-bodying substance.

Gel forms may contain about 5% to about 25% surfactant, about 3% to about 25% polysiloxane having a viscosity of about 1,000 to about 2,500,000 centistokes at 25°C, and about 1% to about 25% of a hair-bodying substance.

Two-phase liquid forms of the product may contain about 5% to about 25% surfactant, about 10% to about 60% polysiloxane having a viscosity of about 1,000 to about 2,500,000 centistokes at 25°C, and about 1% to about 25% of hair-bodying substance.

When the product is a two-phase liquid system, the aqueous phase may comprise one or more of the compositions described in U.S. Pat. No. 3,533,955, the disclosures of which are incorporated herein by reference. In this embodiment the siloxane constitutes the upper oily layer and the hair-bodying agent is incorporated into the aqueous layer. The siloxanes form less stable emulsions in shampoo systems than do the oily components in the compositions of the aforementioned U.S. Pat. No. 3,533,955, and consequently the liquid phases may separate sufficiently soon after using to make the presence of an emulsion destabilizer less important than in the compositions of U.S. Pat. No. 3,533,955.

Optionally, the shampoo composition may further contain from about 0.1 to about 10 weight percent of a hydrophilic thickener to prevent localized deposition of the hair grooming agent, i.e., promote even distribution throughout the hair. Examples of suitable materials are hydroxylpropylmethyl cellulose, proteins, gelatin, methyl cellulose, fumed silicas and polyoxyethylene.

Additionally, these thickeners are used to stabilize gel and liquid preparations of the invention by virtue of the viscosity they impart to the system. Thus, dimethylpolysiloxanes are dispersed throughout the preparation and maintained in suspensions and dispersion by virtue of the viscosity imparted to the external phase by these hydrophilic materials. These systems are thereby stabilized and the separation of the dimethylpolysiloxane into a clear layer is prevented. This is of value to the consumer who may prefer this form of product.

Other water-soluble salts may also be used as hydrophilic thickeners.

Also useful as hydrophilic thickeners are watersoluble salts which are electrolytes well known for this purpose in the art. Exemplary of such electrolytes, to which however the compositions of the invention are not limited, are the alkali-metal halides such as sodium chloride and potassium chloride, the ammonium and substituted ammonium halides, such as ammonium chloride, monoethanolammonium chloride, diethanolammonium chloride, and triethanolammonium chloride, the alkali-metal sulfates, phosphates, citrates and lactates.

The shampoo composition may, of course, also include, if desired such further adjuvants as perfumes or essential oils, dyes and the like to enhance and improve the commercial acceptability of the product. The remainder of the composition usually comprises water.

Suitable lusterizing shampoo compositions may contain the following components in the broad and preferred proportions set forth below:

|  | Percent By Weight, Whole Composition Basis | |
| --- | --- | --- |
|  | Broad | Preferred |
| Surfactant | 5–25 | 10–20 |
| Polydimethylsiloxane | 3–60 | 10–40 |
| Hair-bodying resinous substance | 1–25 | 3–15 |
| Hydrophilic thickener | 0–5 | 2–3 |
| Suds booster | 0–5 | 1–3 |
| Ethanol | 0–40 | 10–25 |
| Water | 20–80 | 20–50 |
| Perfume, colorant, preservative, opacifier, U.V. absorber | q.s. | |

The surfactant system comprises one or more water-soluble surface-active agents, i.e., an anionic surfactant, an amphoteric surfactant, a soap, or a mixture thereof which produces acceptable foam or whose foam is supplemented by a suds improver. Useful anionic detergents are sulfonated and sulfated anionic detergents and in particular the sodium, magnesium, potassium, ammonium and substituted ammonium salts of sulfated fatty alcohols as well as these salts of the sulfonated alkylaryl compounds, and the acyl isethionates, and mixtures thereof.

Amphoteric or ampholytic detergents include N-lauryl-N'-carboxymethyl-N'-(2-hydroxyethyl)ethylenediamine, coco-beta-alanine, the alkali-metal salts of protein-coconut fatty acid condensates, the aminopropionates such as alkyl beta-iminodipropionate represented by $RN(CH_2CH_2COOM)_2$, and alkyl beta-iminopropionate represented by $RNHCH_2CH_2COOM$ wherein R is an aliphatic hydrocarbon radical having about 8 to about 18 carbon atoms and M is a water-solubilizing cation, betaines, sultaines, and the Miranol compounds described in U.S. Pat. Nos. 2,528,378 and 2,781,354, incorporated herein by reference.

Other examples, well known to the art, may be found in the literature such as "Surface Active Agents" by Schwartz and Perry and "Surface Active Agents and Detergents" by Schwartz, Perry and Berch, both Interscience Publishers, New York, New York, the disclosures of which are incorporated herein by reference.

The most preferred detergents are the anionics.

Preferred anionics are the alkyl sulfates wherein the alkyl group may be straight or branched, saturated or unsaturated, and have six to 24 carbon atoms, preferably about 12 to about 18 carbon atoms. Particularly preferred are the monoethanolammonium, diethanolammonium and triethanolammonium alkyl sulfates wherein the alkyl group is a member selected from the group consisting of dodecyl and tetradecyl and mixtures thereof. Also preferred is the triethanolammonium salt of the sulfated condensate of dodecyl - or tetradecyl alcohol or mixtures thereof and about 2 to about 5 molar proportions of ethylene oxide.

Sodium acyl isethionate may be prepared by methods well known to those skilled in the art. Suitable preparatory procedures may be found in U.S. Pat. Nos. 3,320,292, 3,376,229, 3,151,136, 3,383,396, 3,420,857 and 3,420,858.

The alkylbenzenesulfonates useful in the present invention may have a branched alkyl group of about 9 to about 15 carbon atoms such as may be derived from polypropylene as described in U.S. Pat. Nos. 2,477,382 and 2,477,383. Preferably the alkyl group is a straight chain having about 11 to about 15 carbon atoms and the sulfonated phenyl group is randomly positioned along the alkyl chain. Also useful are the alkylbenzenesulfonates described in U.S. Pat. Nos. 2,390,295, 3,320,174 and in Nos. 2,712,530 and 2,723,240.

The term "soap" is used herein in its popular meaning, i.e., the alkali metal salts of aliphatic alkane- or alkenemonocarboxylic acids. The soaps useful herein are the well-known alkali-metal salts of natural or synthetic fatty (alkanoic or alkenoic) acids having about 12 to about 20 carbon atoms, preferably about 12 to about 18 carbon atoms, and may be described as alkali-metal carboxylates of acyclic hydrocarbons having about 12 to about 20 carbon atoms.

Soaps having the fatty acid distribution of coconut oil may provide the lower end of the broad molecular weight range, while soaps having the fatty acid distribution of peanut or rapeseed oil, or their hydrogenated derivatives, may provide the upper end of the broad molecular weight range. It is preferred to use the soaps having the fatty acid distribution of coconut oil or tallow, or mixtures thereof, since these are among the more readily available fats. The proportion of fatty acids having at least 12 carbon atoms in coconut oil soap is about 84%. This proportion will be greater when mixtures of coconut oil and fats such as tallow, palm oil, or non-tropical nut oils or fats are used, wherein the principal chain lengths are $C_{16}$ and higher. The preferred soap for use in the present invention then has at least 84% fatty acids having about 12–18 carbon atoms.

It will be understood that the coconut oil employed for the soap, and for the nonsoap surfactant as well, may be substituted in whole or in part by other "high-lauric" oils, that is, oils or fats wherein at least 50% of the total fatty acids are composed of lauric or myristic acids or mixtures thereof. These oils are generally exemplified by the tropical nut oils of the coconut oil class, such as palm kernel oil, babassu oil, ouricuri oil, tucum oil, cohune nut oil, murumuru oil, jaboty kernel oil, khakan kernel oil, dika nut oil, and for present purposes ucuhuba butter, a vegetable triglyceride high in myristic acid esters.

A preferred soap is a mixture of about 15% to about 25% coconut oil and about 75% to about 85% tallow. These mixtures contain about 95–96% fatty acids having about 12 to about 18 carbon atoms. The soap may be prepared from coconut oil, in which case the fatty acid content is about 84% of $C_{12}$–$C_{18}$ chain length.

The soaps may contain unsaturation in accordance with the commercially acceptable standards. Excessive unsaturation is normally avoided.

The soaps may be made by the well-known kettle boiling process from natural fats and oils such as tallow or coconut oil or their equivalents, by boiling with an alkali-metal hydroxide, using procedures well known to those skilled in the art. Alternatively the soaps may be made by neutralizing fatty acids, such as lauric ($C_{12}$), myristic ($C_{14}$), palmitic ($C_{16}$), or stearic ($C_{18}$) acids with an alkali-metal hydroxide or carbonate.

The amphoteric detergents may include any of the high-foaming quaternary cycle compounds disclosed in the aforementioned U.S. Pat. Nos. 2,528,378 and 2,781,354. Of special interest are the quaternary cycloimidates having the general structure.

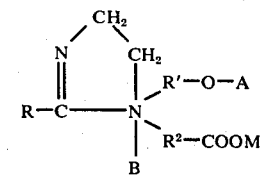

wherein
R is an aliphatic hydrocarbon radical having about 9 to about 17 carbon atoms,
R' and R² are each independently
a. a divalent alkylene radical having 1 to 4 carbon atoms,
b. a hydroxy-substituted divalent alkylene radical having 2 to 4 carbon atoms,
c. a divalent alkylene radical having 2–4 carbon atoms wherein said alkylene radical contains an ether or a keto linkage, and
d. a hydroxy-substituted divalent alkylene radical having 2–4 carbon atoms wherein said alkylene radical contains an ether or a keto linkage,
M is a water-solubilizing cation,
A is
a. M,
b. —CH₂COOM
c. —C₂H₄OCH₂COOM or
d. —C₂H₄COOM, and
B is
a. OH,
b. $C_{12}H_{25}OSO_3$—, or
c. $C_{12}H_{25}$—$C_6H_4$—$SO_3$—

Particularly preferred amphoteric surfactants are the substituted quaternary hydroxy cycloimidinic acid alkali metal alcoholates described in U.S. Pat. No. 2,528,378 and which have the generic structure:

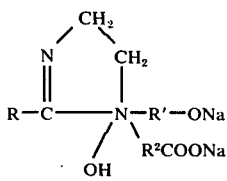

wherein R is an aliphatic hydrocarbon radical having about 9–17 carbon atoms, R' and R² represent divalent alkylene groups having 1 to 4 carbon atoms, and may be the same or different.

The most preferred of the amphoteric surfactants are the substituted quaternary hydroxy cycloimidinic acid alkali metal alkoxymethyl carboxylates described in U.S. Pat. No. 2,781,354, and which have the generic structure:

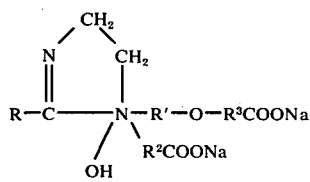

wherein R is an aliphatic hydrocarbon radical having about 9 to about 17 carbon atoms, R' and R² are as defined above, and R³ is a divalent alkylene group having 1 to 2 carbon atoms.

A useful compound is one having the foregoing structure wherein R has 11 carbon atoms, R' has 2 carbon atoms and R² and R³ each have 1 carbon atom.

The betaines may have the structure

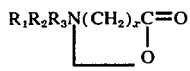

wherein $R_1$ is an alkyl group having about 12 to about 18 carbon atoms or a mixture thereof, $R_2$ and $R_3$ are independently lower alkyl groups having 1 to 3 carbon atoms, and N is an integer from 1 to 4. Specific betaines useful in the products of the invention are for example alpha-(tetradecyldimethylammonio) acetate, beta-(hexadecyldiethylammonio)propionate, and gamma (dodecyldimethylammonio)butyrate.

The sultaines may have the structure

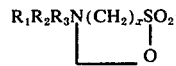

wherein $R_1$, $R_2$, $R_3$ and $x$ are defined as above. Specific useful sultaines are for example 3-(dodecyldimethylammonio) propane-1-sulfonate, and 3-(tetradecyldimethylammonio)ethane-1-sulfonate.

The the term "water-solubilizing cation" is meant any cation which, when associated with the detergent anion, does not result in an insoluble compound. A cation suitable as the cation of some of the aforementioned surfactants may not be suitable for others, as for example calcium and magnesium cations, which are appropriate for many of the nonsoap surfactants but are not suitable as cations in the compositions of the instant invention when the surfactant is predominantly soap.

Among the cations which may be associated with the surfactants, subject to the aforementioned limitation, are sodium, potassium, lithium (alkali metals, group I of the Periodic Table), calcium, magnesium (group II of the Periodic Table), ammonium, and substituted ammonium ions. Among the substituted ammonium ions there may be mentioned the methyl-, dimethyl-, trimethyl-, tetramethyl-, ethyl-, diethyl-, triethyl-, tetraethyl-, monoethanol-, diethanol-, triethanolammonium, and morpholinium ions.

Compatible mixtures of the foregoing types, i.e., anionics, amphoterics, or soap, or mixtures within each type, may be used.

The polydimethylsiloxanes suitable for use in the present inventon are the well-known dimethylsiloxane polymers which may generally be represented by the structure:

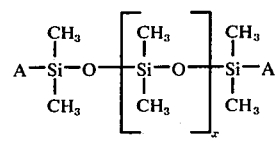

wherein $x$ is an integer from about 220 to about 2400, and A is $CH_3$, $CH_3O, C_2H_5O$ or $C_3H_7O$.

While the structure of the polydimethylsiloxanes is illustrated as having the above molecular configuration, it will be understood that the commercially available grades may be mixtures of polysiloxanes wherein the above structure predominates. Moreover, values assigned to $x$ in the present application are average values.

The polydimethylsiloxane polymers may be made by procedures well known by those skilled in the art, and may be made at varying degrees of polymerization, to provide viscosities of from example 0.65 to 2,500,000 centistokes.

Suitable preparative methods are found in the text, "An Introduction to the Chemistry of Silicones" by E. G. Rochow, second Edition, 1951, John Wiley & Sons, Inc. New York.

In one method described, for the preparation of methyl-blocked silicones, elemental silicon is reacted with methyl chloride under the influence of copper metal catalyst to produce dimethyldichlorosilocane, along with certain by-products. The dimethyldichlorosilocane is hydrolyzed and polymerized to form the desired polydimethylsiloxane.

Methods for the preparation of alkoxy end-blocked polysiloxanes are found in U.S. Pat. No. 2,415,389, which is incorporated herein by reference.

A discussion of silicones in general may be found in Kirk-Othmer, "Encyclopedia of Chemical Technology", Volume 18, 1969, Interscience Publishers, particularly at pages 221–248.

The polydimethylsiloxanes employed in the Examples herein are members of the Viscasil series. Viscasil is a trademark of the General Electric Company.

Mixtures of the aforementioned polysiloxanes having different viscosities and chain lengths may be employed.

Resinous materials, in general, tend to impart bodying or set holding to the hair. Suitable resins for purposes of the present invention would include shellac, wood rosins and the $C_1$ to $C_6$ esters thereof, the wood rosins and esters preferably having a softening point of between about 96°C to about 125°C and A Gardner-Holt viscosity of between about 20 and 40. Preferred embodiments of these rosins are their $C_1$ to $C_6$ esters and polymerized and dimerized rosins (softening point 98°–106°C, acid number 140 minimum), hydrogenated rosin (softening point 69°–80°C, acid number 158 minimum) and hydrogenated methyl ester of rosin (boiling point 350°–380°C preferably 360°–364°C, acid number 7 minimum). Other suitable hair-bodying are sucrose acetate isobutyrate, polyvinyl ethyl ether resin having a molecular weight of from about 10,000–750,000, alkyl resins having a preferred molecular weight of from about 10,000–50,000, polyketone resins having a preferred average molecular weight of from about 500–1,000, most preferably 600–800, vinyl acetate resins having an average molecular weight of from about 8,000–15,000, acrylic resins having an average molecular weight of from about 10,000–150,000, and mixtures thereof.

Waxy materials tend to impart bodying and conditioning effects to the hair. Suitable waxy materials would include, but are not limited to, cocoamide (preferably having a melting point of 80°–90°C), ethylene-maleic anhydride resins, ethoxylated lanolin containing about 5 to about 25 moles of ethylene oxide, stearyl amide (preferably having a melting point of 95°–110°C), ethoxylated higher fatty alcohols, preferably $C_{14}$–$C_{30}$ having 2 to 4 moles of ethylene oxide, and the like. Liquid grooming agents such as lanolin alcohols (preferably having a saponification value of about 144–150), mineral oil fractions having a Saybolt viscosity of about 50 to about 360 sec., and the like, tend to impart conditioning and ease of combing effects to the hair.

Preferred hair bodying agents are the above defined wood rosins, sucrose acetate isobutyrate, a copolymer of vinyl acetate and crotonic acid having a molecular weight of about 12,000, an ethylene-maleic anhydride copolymer cross linked with vinyl crotonate, having a viscosity of about 160,000 cps, polyketone and shellac used alone or in combinations, such as wood rosins — polyketone, and sucrose acetate isobutyrate — polyketone at ratios from about 1:9 to about 1:1, most preferably 1:5 to 5:1. Combinations of hair grooming agents are often desired because of the balance of benefits they provide.

The use of a suds booster is optional. When desired, the suds boosters useful in the shampoo compositions of the invention may be selected from the compounds well known for their general and specific effects. For example, there may be used the fatty amides, such as lauric, myristic, and palmitic amides, monoethanolamides, diethanolamides, and isopropanolamides. Where suitable, the stearic derivatives may be used. Mixed lauric and myristic derviatives of the aforementioned amides and substituted amides, as well as the coconut oil and tallow derivatives are useful. Lauryl alcohol and myristyl alcohol find utility with the alkyl sulfate detergents. Also useful are the sulfoxides, amine oxides, and phosphine oxides having one long ($C_{12}$–$C_{18}$) alkyl chain, the particular compounds being well known in the art. It will be understood that the suds booster, when desired, will be selected with due regard to the detergent species with which it is to be associated.

The invention may be more fully understood by reference to the following examples, which illustrate, but by no means limit the scope of the invention.

EXAMPLE 1

The following compositions are within the invention.

|  | Percent By Weight | | | | | |
| --- | --- | --- | --- | --- | --- | --- |
|  | A | B | C | D | E | F |
| Polydimethylsiloxane, 1,000 centistokes[a] | 20.0 | | | | | |
| Polydimethylsiloxane, 5,000 centistokes[a] | | 15.0 | | | | |
| Polydimethylsiloxane, 10,000 centistokes[a] | | | 10.0 | | | 10.0 |
| Polydimethylsiloxane, 30,000 centistokes[a] | | | | 7.0 | | |
| Polydimethylsiloxane, 2,500,000 centistokes[a] | | | | | 3.0 | |
| Shellac, bleached, dewaxed | | | 5.0 | | | 5.0 |
| Sucrose acetyl isobutyrate[b] | | 5.0 | | 7.0 | | |
| Cationic cellulose[c] | 4.0 | | | | | |
| Polymerized rosin[d] | | | | | 5.0 | |
| Ethanol | | 20.0 | 30.0 | 20.0 | 20.0 | 20.0 |
| Methyl cellulose, 60 NG[e] | 3.0 | 3.0 | 3.0 | 3.0 | 3.0 | 3.0 |
| Triethanolammonium lauryl sulfate | | | 16.0 | 10.0 | 5.0 | |
| Potassium lauryl.E.O. sulfate[f] | 25.0 | | | | | |
| Ammonium alkylbenzenesulfonate[g] | | | | | | 20.0 |
| Lauric diethanolamide | | | | | | 2.0 |
| N-alkyl-beta-alanine[h] | | 20.0 | | | | |
| Alkyl dimethyl amine oxide[h] | | | 1.5 | | | |
| Perfume | 0.5 | 0.5 | 0.5 | 0.5 | 0.5 | 0.5 |
| Triethanolamine, q.s. to pH 6.2 | | | | | | |
| Water, q.s. to 100% | | | | | | |
|  | 100 | 100 | 100 | 100 | 100 | 100 |

[a] Figures are viscosity at 25°C in centistokes.
[b] SAIB 90, obtainable from the Eastman Kodak Co.
[c] "Polymer JR", trademark of the Union Carbide Corp. having the structural formula:

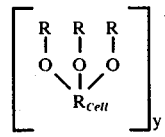

where $R_{Cell}$ is the residue of an anhydroglucose unit

-continued ($C_6H_{10}O_5$), the R's may be the same or different and each R individually represents a substituent group of the formula given hereinbelow, and y represents the degree of polymerization and is an integer having a value of from about 50 to about 20,000, or more, and preferably from about 200 to about 5,000.

In the above structural formula each R individually represents a substituent group of the general formula:

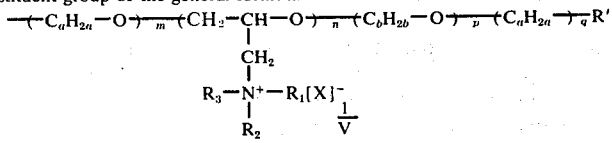

wherein:
a is an integer having a value of from 2 to 3;
b is an integer having a value of from 2 to 3;
c is an integer having a value of from 1 to 3;
m is an integer having a value of from zero to 10;
n is an integer having a value of from zero to 3;
p is an integer having a value of from zero to 10;
q is an integer having a value of from zero to 1;
R' is a member selected from the group consisting of

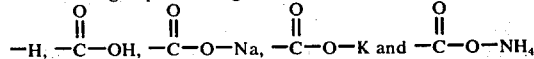

with the proviso that when q is zero then R' is —H;

$R_1$, $R_2$ and $R_3$, taken individually, represent a member selected from the group consisting of alkyl, aryl, aralkyl, alkaryl, cycloalkyl, alkoxyalkyl and alkoxyaryl radicals where each of $R_1$, $R_2$ and $R_3$ can contain up to 10 carbon atoms, with the proviso that when said member is an alkoxyalkyl radical there are at least 2 carbon atoms separating the oxygen atom from the nitrogen atom, and with the further proviso that the total number of carbon atoms in radicals represented by $R_1$, $R_2$ and $R_3$ is from 3 to 12;

$R_1$, $R_2$ and $R_3$, taken together, represent along with the nitrogen atom to which they are attached a member selected from the group consisting of pyridine, α-methylpyridine, 3,5-dimethylpyridine, 2,4,6-trimethylpyridine, N-methyl piperidine, N-ethyl piperidine, N-methyl morpholine and N-ethyl morpholine;

X is an anion such as chloride, bromide, iodide, sulfate, methylsulfate, sulfonate, nitrate, phosphate, acetate, etc., and V is an integer which is equal to the valence of X;

The average value of n per anhydroglucose unit is from about 0.01 to about 1 and preferably from about 0.1 to about 0.5; and The average value of m+n+p+q per anhydroglucose unit is from about 0.01 to about 4, more preferably from about 0.1 to about 2.5, and most preferably from about 0.8 to about 2.

(d)Softening point 98°–106°C, acid No. 140.
(e)50,000 centipoises.
(f)"E.O." = average of 3.1 oxyethylene units.
(g)Alkyl group is straight chain mixture averaging about 13 carbon atoms.
(h)"Alkyl" = a mixture of alkyl groups having the molecular distribution of coconut oil fatty acids.

EXAMPLE 2

Following is an example of a two-phase liquid shampoo within the invention.

| | Percent By Weight, Whole Composition Basis |
|---|---|
| Oil Phase | |
| Polydimethylsiloxane, 10,000 centistokes viscosity. | 40.00 |
| Aqueous Phase | |
| Triethanolammonium lauryl sulfate (solids) | 9.30 |
| Cocosulfobetaine | 5.98 |
| Hydrolyzed Collagen | 1.72 |
| Perfume | 0.36 |
| Preservatives | 0.14 |
| Opacifier | 0.07 |
| Dimerized rosin, Na salt(a) | 5.00 |
| U.V. absorber | 0.07 |
| Colorant | 0.35 |
| SDA alcohol No. 40 (190 proof ethanol) | 14.10 |
| Water | 22.91 |
| | 100.00 |

(a)Softening point 69°–80°C, acid No. 140 before neutralization.

EXAMPLE 3

This example illustrates the substantial lack of antifoam effect of a polydimethylsiloxane within the invention. For example, a liquid two-phase shampoo composition of the type illustrated in Example 2 but without the dimerized rosin exhibits the following comparative foam volumes at varying siloxane weight proportions by cylinder foam tests on 2% solutions of the shampoo compositions. The siloxane employed has a viscosity of 10,000 centistokes.

TABLE 1

| | Popular Commercial Shampoos | | | Shampoos with Indicated Percentages of Polydimethylsiloxane | | | |
|---|---|---|---|---|---|---|---|
| | A | B | C | 20% | 30% | 40% | 50% |
| Foam Volume Immediately After Shaking, ml | 360 | 640 | 810 | 850 | 800 | 750 | 660 |
| Foam Volume After 5 Minutes' Standing, ml | 75 | 540 | 700 | 725 | 685 | 645 | 570 |

The foregoing data show that polydimethylsiloxane having a viscosity of 10,000 centistokes has only a light anti-foam action in proportions up to 50% by weight in a shampoo based on a mixture of triethanolammonium lauryl sulfate and cocodimethyl sulfobetaine.

EXAMPLE 4

The following composition is within the invention.

| Mix I | Percent By Weight |
|---|---|
| Alcohol, SDA No. 40, anhydrous | 17.25 |
| Shellac, dewaxed, white bleached | 6.80 |
| Cocodiethanolamide[(a)] | 1.81 |
| Perfume | 0.25 |
| Hydroxypropylmethylcellulose (Methocel 65HG, 4000 cps) | 2.73 |
| Mix II | |
| Distilled water and HCl q.s. to pH 5.8 | 15.46 |
| Ethylenediamine tetraacetic acid | 0.20 |
| Triethanolammonium lauryl sulfate at 46% active | 45.50 |
| Polydimethylsiloxane, 10,000 csks. | 10.00 |
| | 100.00 |

[(a)]N-diethanol alkaneamide wherein the alkane portion is a mixture having the chain-length distrubution of coconut oil fatty acids.

To prepare the foregoing composition, the components of Mix I are mixed together in the order shown. The alcohol, shellac, and diethanolamide are warmed, to facilitate solution. The Methocel is then added and maintained in suspension by rapid agitation. Next, a solution is made of the first three components of Mix II, and added to Mix I. The pH is adjusted to 5.8 prior to complete hydration and swelling of the Methocel. After 1 hour's stirring, during which time the Methocel has substantially completely swelled, the polydimethylsiloxane is slowly stirred into the mixture.

The above-described shampoo is a slightly opaque, nearly translucent, slightly acidic, flowing gel with minute globules of polydimethylsiloxane held in suspension. The globules of polydimethylsiloxane are two small to be discerned with the unaided eye. The product is stable when stored for four weeks at room temperature, there being no evidence of creaming or syneresis prior to that period of time.

In vitro shampoo tests of the above-described product using switches of hair from human heads, show excellent luster enhancement on blond and gray hair, and slightly less (rated good) enhancement on dark brown hair. In all cases there is a noticeable deepening or enrichment of hair color, which is typical of brilliantine applications.

The hair switches washed with the foregoing shampoo composition are easy to comb, with a slight tendency towards grouping (comb tracks). The foam performance is less than desirable at the initial application, but satisfactory with the second application.

When compared with a popular commercial shampoo which contains no lusterizing or hair-bodying agent on the undamaged hair of female human subjects, the above-described shampoo exhibits better combing, styling, set-holding characteristics, and luster, which are apparent after two to three days of normal wear and still perceptible after an application of hair spray. The lusterizing effect is more evident on light-colored hair, e.g., gray, blond, salt and pepper, than on dark colored hair. No lusterizing effect is noted on hair that has been heavily bleached and toned, probably due to absorption of the siloxane by the porous hair strands resulting from the bleaching process. However, in tests with this type of hair, a luster improvement is noted in areas of new growth of undamaged hair.

It is believed that the deposition of the polydimethylsiloxane and shellac is due to a dilution-deposition mechanism described hereinbefore, and is dependent upon the precipitation of the aforementioned components upon dilution. Precipitation upon dilution of the composition of Example 4 is dependent upon the pH. If the pH is lowered to about 5 or below, the polydimethylsiloxane and shellac precipitate from the composition without dilution, and at pH levels above 6.5 there is no precipitation on dilution and little luster is imparted to hair.

EXAMPLE 5

The following composition is within the invention.

| | Percent By Weight |
|---|---|
| Polydimethylsiloxane, visc. 10,000 centistokes | 5.0 |
| Polymer - a cationic amino cellulose, visc. 400–500 cps | 3.0 |
| Sodium chloride | 5.0 |
| Ammonium lauryl sulfate (28% solution) | 50.0 |
| Perfume | 0.5 |
| Colorant (FD&C Blue No. 1) (2% solution) | 0.1 |
| Water | 36.4 |
| | 100.0 |

The product is a translucent flowing gel, having a pH of 6.25 at 25°C.

EXAMPLE 6

Following is an example of a composition containing cocomonoethanolamide as suds booster and triethanolammonium chloride as a thickening agent.

| | Percent by Weight |
|---|---|
| Polydimethylsiloxane, visc. 60,000 centistokes | 5.0 |
| Polymer - a cationic amino cellulose, visc. 400–500 cps. | 3.0 |
| Triethanolammonium chloride | 15.8 |
| Ammonium lauryl sulfate (28% solution) | 50.0 |
| Cocomonoethanolamide[(a)] | 2.5 |
| Perfume | 0.5 |
| Colorant (FD&C Green No. 5) (0.5% solution) | 0.1 |
| Water | 23.1 |
| | 100.0 |

[(a)]as defined in Example 4.

The product is a viscous flowing liquid having a pH of 6.25 at 25°C.

EXAMPLE 7

A female human subject having brown hair of medium length shampoos her hair with the composition of Example 1-D. The hair is wet with water to the point of saturation and the shampoo composition is poured on the hair. Foam is generated by working the hair with the fingers and hands, and massaging the scalp with the tips of the fingers, adding more water as desired. After washing, the hair is rinsed, removing substantially all foaming substances. The washing and rinsing steps are repeated. The hair, after combing and drying, appears lustrous without a tactile feel of oiliness.

Having described the invention, persons skilled in the art will be aware of modifications within the spirit thereof, and the invention is to be limited only within the scope of the appended claims.

What is claimed is:

1. A lusterizing shampoo composition comprising:
   i. about 5% to about 25% of an anionic or amphoteric surfactant,
   ii. about 3% to about 60% of a polydimethylsiloxane having a viscosity of about 1000 to about 2,500,000 centistokes at 25°C,
   iii. about 1% to about 25% of a hair-bodying agent selected from the group consisting of:
      A. A wood rosin having a softening point of about 96°C to about 125°C and a Gardner-Holt viscosity of between about 20 and 40;
      B. Bleached and dewaxed shellac;
      C. Sucrose acetate isobutyrate; and
      D. A cationic amino cellulose compound; and
   iv. about 30% to about 91% of a solvent, said solvent comprising 0% to about 50% ethanol, basis by weight of said solvent, the balance being water.

2. A lusterizing shampoo composition in accordance with claim 1 wherein said surfactant is triethanolammonium lauryl sulfate.

3. A lusterizing shampoo composition in accordance with claim 1 wherein said surfactant is the sodium salt of the sulfated condensate of one mole of lauryl or myristyl alcohol and an average of about 1 to about 3 molar proportions of ethylene oxide.

4. A lusterizing shampoo composition in accordance with claim 1 wherein said surfactant is a quaternary cycloimidate having the structure:

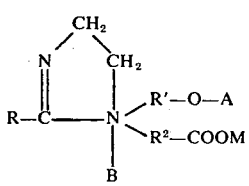

wherein
R is an aliphatic hydrocarbon radical having about 9 to about 17 carbon atoms,
R' and R² are each independently
   a. a divalent alkylene radical having 1 to 4 carbon atoms,
   b. a hydroxy-substituted divalent alkylene radical having 2 to 4 carbon atoms,
   c. a divalent alkylene radical having 2-4 carbon atoms wherein said alkylene radical contains an ether or a keto linkage, and
   d. a hydroxy-substituted divalent alkylene radical having 2-4 carbon atoms wherein said alkylene radical contains an ether or a keto linkage,
M is a water-solubilizing cation,
A is
   a. M,
   b. —CH₂COOM
   c. —C₂H₄OCH₂COOM or
   d. —C₂H₄COOM, and
B is
   a. OH
   b. C₁₂H₂₅—OSO₃⁻ or
   c. C₁₂H₂₅—C₆H₄—SO₃⁻.

5. A lusterizing shampoo composition in accordance with claim 1 wherein said surfactant is a compound having the structure:

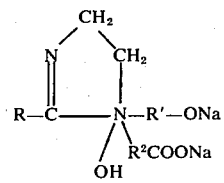

wherein R is an aliphatic hydroxycarbon radical having about 9 to about 17 carbon atoms, R' and R² are divalent alkylene groups having 1 to about 4 carbon atoms, and may be the same or different.

6. A lusterizing shampoo composition in accordance with claim 1 wherein said surfactant is a compound having the structure:

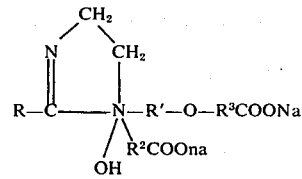

wherein R is an aliphatic hydrocarbon radical having about 9 to about 17 carbon atoms R' and R² are divalent alkylene groups having 1 to about 4 carbon atoms, and may be the same or different, and R³ is a divalent alkylene group having 1 or 2 carbon atoms.

7. A lusterizing shampoo composition in accordance with claim 1 wherein said polydimethylsiloxane has a viscosity of about 5,000 centistokes, said viscosity being measured at 25°C.

8. A lusterizing shampoo composition in accordance with claim 1 wherein said polydimethylsiloxane has a viscosity of about 10,000 centistokes, said viscosity being measured at 25°C.

9. A lusterizing shampoo composition in accordance with claim 1 wherein said polydimethylsiloxane has a viscosity of about 60,000 centistokes, said viscosity being measured at 25°C.

10. A lusterizing shampoo composition in accordance with claim 1 wherein said hair-bodying agent is bleached and dewaxed shellac.

11. A lusterizing shampoo composition in accordance with claim 1 wherein said hair-bodying agent is sucrose acetate isobutyrate.

12. A lusterizing shampoo composition in accordance with claim 1 wherein said hair-bodying agent is a wood rosin.

13. A lusterizing shampoo composition in accordance with claim 1 additionally comprising from 0.1 to about 10% by weight of a hydrophilic thickening agent.

14. A lusterizing shampoo composition in accordance with claim 13 wherein said thickening agent is triethanolammonium chloride.

15. A lusterizing shampoo composition in accordance with claim 13 wherein said thickening agent is hydroxypropylmethyl cellulose.

16. A process for imparting luster to hair on the human head, comprising washing said hair with the shampoo composition defined in claim 14 in a sufficient amount for depositing on the hair said polydimethylsiloxane and to impart visual luster with substantially no tactile feel of oiliness, and rinsing to thereby remove substantially all foaming components from the hair.

* * * * *

UNITED STATES PATENT OFFICE
CERTIFICATE OF CORRECTION

PATENT NO. : 3,964,500
DATED : June 22, 1976
INVENTOR(S) : Raymond Drakoff

It is certified that error appears in the above-identified patent and that said Letters Patent are hereby corrected as shown below:

Column 7, Line 49, change "N" to --x--.

Signed and Sealed this

Thirtieth Day of November 1976

[SEAL]

Attest:

RUTH C. MASON
*Attesting Officer*

C. MARSHALL DANN
*Commissioner of Patents and Trademarks*